United States Patent
Zhao et al.

(10) Patent No.: US 10,289,148 B2
(45) Date of Patent: May 14, 2019

(54) OPERATING DEVICE AND OPERATING METHOD

(71) Applicant: BOE TECHNOLOGY GROUP CO., LTD., Beijing (CN)

(72) Inventors: Kai Zhao, Beijing (CN); Yu Gu, Beijing (CN); Ying Zhang, Beijing (CN); Hongli Ding, Beijing (CN); Yifei Zhang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 0 days.

(21) Appl. No.: 15/574,960

(22) PCT Filed: May 4, 2017

(86) PCT No.: PCT/CN2017/083037
§ 371 (c)(1),
(2) Date: Nov. 17, 2017

(87) PCT Pub. No.: WO2017/193866
PCT Pub. Date: Nov. 16, 2017

(65) Prior Publication Data
US 2018/0173268 A1 Jun. 21, 2018

(30) Foreign Application Priority Data

May 13, 2016 (CN) .......................... 2016 1 0320205

(51) Int. Cl.
*G05G 1/00* (2006.01)
*G05G 5/02* (2006.01)
(Continued)

(52) U.S. Cl.
CPC ................. *G05G 5/02* (2013.01); *A61G 5/10* (2013.01); *G05G 9/047* (2013.01); *G06F 3/00* (2013.01);
(Continued)

(58) Field of Classification Search
CPC .. G05G 5/02; G05G 9/047; G05G 2009/0474; A61G 5/10; A61G 2203/14; G06F 3/00; A61B 5/1101; G05B 19/042
See application file for complete search history.

(56) References Cited

U.S. PATENT DOCUMENTS 4,996,977 A   3/1991   Tiedeken
2011/0168478 A1   7/2011   Kuo et al.
(Continued)

FOREIGN PATENT DOCUMENTS

CN   101612044 A   12/2009
CN   101920066 A   12/2010
(Continued)

OTHER PUBLICATIONS

Search Report for International Chinese Patent Application No. PCT/CN2017/083037 dated Aug. 3, 2017.
(Continued)

*Primary Examiner* — Jake Cook
(74) *Attorney, Agent, or Firm* — Calfee, Halter & Griswold LLP

(57) ABSTRACT

An operating device and an operating method are disclosed. The operating device includes a processing assembly and a control assembly. The control assembly includes a control body, an auxiliary unit and a collecting unit. The auxiliary unit is arranged on the control body, a limb of a user is put on said auxiliary unit, and the collecting unit is arranged on the limb of the user. The collecting unit is configured to collect trembling signals indicating limb trembling of the user, and transmit the trembling signals to the processing assembly. The processing assembly is configured to generate driving signals according to the trembling signals and transmit the driving signals to the auxiliary unit. The auxiliary unit is configured to keep a motion state of said auxiliary
(Continued)

unit to be the same as a limb trembling state of the user according to said driving signals.

20 Claims, 8 Drawing Sheets

(51) Int. Cl.
*A61G 5/10* (2006.01)
*G05G 9/047* (2006.01)
*G06F 3/00* (2006.01)
*A61B 5/11* (2006.01)
*G05B 19/042* (2006.01)

(52) U.S. Cl.
CPC ......... *A61B 5/1101* (2013.01); *A61G 2203/14* (2013.01); *G05B 19/042* (2013.01); *G05G 2009/0474* (2013.01)

(56) References Cited

U.S. PATENT DOCUMENTS

| | | | |
|---|---|---|---|
| 2013/0297022 | A1 | 11/2013 | Pathak |
| 2017/0020704 | A1* | 1/2017 | Wu ........................ A61F 4/00 |

FOREIGN PATENT DOCUMENTS

| | | |
|---|---|---|
| CN | 202943642 U | 5/2013 |
| CN | 103906483 A | 7/2014 |
| CN | 105232249 A | 1/2016 |
| CN | 105759657 A | 7/2016 |
| CN | 205608439 U | 9/2016 |

OTHER PUBLICATIONS

First Office Action for Chinese Patent Application No. 201610320205.7 dated Nov. 26, 2017.

* cited by examiner

OPERATING DEVICE AND OPERATING METHOD

RELATED APPLICATION

The present application is the U.S. national phase entry of PCT/CN2017/083037, with an international filing date of May 4, 2017, which claims the benefit of Chinese Patent Application No. 201610320205.7, filed on May 13, 2016, the entire disclosures of which are incorporated herein by reference.

TECHNICAL FIELD

The present disclosure relates to the field of electronic technology and in particular to an operating device and an operating method.

BACKGROUND

With the rapid development of electronic technologies, operating devices have been more and more widely used. An operating device is a device controlled by a user to achieve target actions. Operating devices make people's life more convenient and comfortable. For example, wheelchairs, as operating devices, bring great convenience to the disabled, the weak, and the elderly.

An operating device in the prior art usually comprises a processing assembly and a control assembly. The control assembly may be controlled by the processing assembly, or it may be directly subjected to limb manipulations of a user. In cases where the control assembly is controlled by the processing assembly, the processing assembly can receive instructions triggered by the user and transmits said instructions to the control assembly which then controls the operating device to achieve target actions according to said instructions. In cases where the control assembly is directly operated by limbs of the user, it may achieve corresponding target actions under limb operations of the user. In cases where the operating device is a wheelchair, the control assembly, if not being directly operated by the limbs of the user, may move forward or backward according to the instructions sent by the processing assembly. In the meantime, the hands of the user can be put on the control assembly.

But when the user suffers from morbid tremor, the arm of the user may tremble irregularly, and thus the hands put on the control assembly will have an acting force on the control assembly. Finally, the control assembly will control the operating device to achieve a new action (not consistent with the operation intention of the user) under said force. Therefore, the operating device is poorly reliable.

SUMMARY

In order to overcome some or all of the above problems, the present disclosure advantageously provides an operating device and an operating method.

According to an aspect of the present disclosure, an operating device is provided, which comprises a processing assembly; and a control assembly comprising a control body, an auxiliary unit and a collecting unit; wherein the auxiliary unit is arranged on the control body, a limb of a user is put on said auxiliary unit, and the collecting unit is arranged on the limb of the user; and wherein said collecting unit is configured to collect trembling signals indicating limb trembling of the user, and transmit said trembling signals to the processing assembly; said processing assembly is configured to generate driving signals according to said trembling signals and transmit said driving signals to the auxiliary unit; said auxiliary unit is configured to keep a motion state of said auxiliary unit to be the same as a limb trembling state of the user according to said driving signals.

In certain exemplary embodiments, said auxiliary unit may comprise: a handrail, a baseboard, a hinge unit and at least three deflection units. Said handrail is provided with a handrail chassis and a joystick connected to said handrail chassis, a length direction of said joystick is perpendicular to a surface of the handrail chassis, said joystick is configured to receive limb operations of the user, and the surface of the handrail chassis is parallel to a surface of the baseboard; said hinge unit is located at the middle of a column formed by the handrail chassis and the baseboard and is hinged to the handrail chassis, and said hinge unit is fixedly connected to the baseboard; said at least three deflection units are inside the column formed by the handrail chassis and the baseboard and are distributed around the hinge unit, and they are configured to deflect according to the driving signals, so that the motion state of the handrail remains to be the same as the limb trembling state of the user.

In certain exemplary embodiments, each of said deflection units include a rotating sub-unit and a driving sub-unit, wherein said rotating sub-unit is in point and plane contact with the handrail chassis, and is in fixed connection to said driving sub-unit, said driving sub-unit is configured to rotate according to the driving signals so as to drive said rotating sub-unit to deflect.

In certain exemplary embodiments, said rotating sub-unit comprises a cam, and said driving sub-unit comprises a motor bearing and a motor arranged in said motor bearing; said motor bearing is fixedly connected to said baseboard, and said motor is configured to rotate according to the driving signals so as to drive said cam to deflect.

In certain exemplary embodiments, said hinge unit comprises a hinge frame, and a hinge bearing is provided between said hinge frame and said handrail chassis, said hinge bearing is fixedly connected to said handrail chassis, said hinge bearing is a column with a boss, and a center of a side of said boss facing away from the handrail chassis is concave in shape.

In certain exemplary embodiments, said hinge frame comprises a first connector, a second connector and a third connector connected in turn; wherein the first connector is spherical in shape, and is in contact with the concave center of the boss;

the second connector is cylindrical in shape, and a height direction thereof is perpendicular to the surface of the handrail chassis; and the third connector is cylindrical in shape, and a height direction thereof is perpendicular to the surface of the baseboard, the third connector being fixedly connected to the baseboard and being at the middle of the baseboard.

In certain exemplary embodiments, said auxiliary unit further comprises a protection unit made of an elastic material, wherein said protection unit is arranged between the handrail chassis and the baseboard, and encloses the hinge unit and the at least three deflection units.

In certain exemplary embodiments, a bolt hole is provided on the baseboard, which is penetrated by a bolt so that said auxiliary unit is fixed on the control body.

In certain exemplary embodiments, said processing assembly is further configured to transmit a pre-set adjustment signal to said auxiliary unit; and said auxiliary unit is further configured to make the motion state of said auxiliary unit to be inconsistent with the limb trembling state of the user according to said adjustment signal.

In certain exemplary embodiments, said collecting unit can comprise a patch sensor.

In certain exemplary embodiments, the surface of the handrail chassis and the surface of the baseboard can both be circular.

In certain exemplary embodiments, said baseboard can be made of aluminum.

In certain exemplary embodiments, said processing assembly can further be configured to transmit pre-obtained autonomous motion signals to the control body after transmitting the driving signals to the auxiliary unit, so that the operating device can achieve the target action indicated by the autonomous motion signals, said autonomous motion signals indicating the intention of operation of the user.

In certain exemplary embodiments, said operating device is a wheelchair.

According to a second aspect of the present disclosure, an operating method is provided, which is carried out by any of the above-mentioned operating device, said method comprises:

collecting trembling signals indicating limb trembling of the user;

generating driving signals according to said trembling signals;

keeping a motion state of the auxiliary unit to be the same as a limb trembling state of the user according to said driving signals.

In certain exemplary embodiments, said method further comprises making the motion state of said auxiliary unit to be inconsistent with the limb trembling state of the user according to a pre-set adjustment signal.

In certain exemplary embodiments, said collecting trembling signals indicating limb trembling of the user comprises:

detecting whether a frequency of limb motion of the user is within a pre-set range;

determining signals generated by said limb motion as the trembling signals if the frequency of limb motion of the user is within the pre-set range.

In certain exemplary embodiments, said collecting trembling signals indicating limb trembling of the user comprises:

collecting trembling signals indicating limb trembling of the user through a patch sensor.

In certain exemplary embodiments, said method may further comprise:

achieving the target action indicated by the autonomous motion signals according to the pre-obtained autonomous motion signals, said autonomous motion signals indicating the intention of operation of the user.

It shall be appreciated that the above generalization and the detailed descriptions that will be given below are exemplary, and they do not limit the contents of the present disclosure.

BRIEF DESCRIPTION OF THE DRAWINGS

In order to describe the technical solutions in embodiments of the present disclosure more clearly, the drawings that will be used for describing the embodiments will be introduced briefly below. The same reference sign represents the same unit or element throughout the document.

It shall be pointed out that these drawing and text descriptions do not intend to limit the scope of the concept of the present disclosure in any way.

DETAILED DESCRIPTION

In order to make the technical solutions and advantages of the present disclosure clearer, embodiments of the present disclosure will be described in further detail below with reference to the drawings.

Figure 1A:
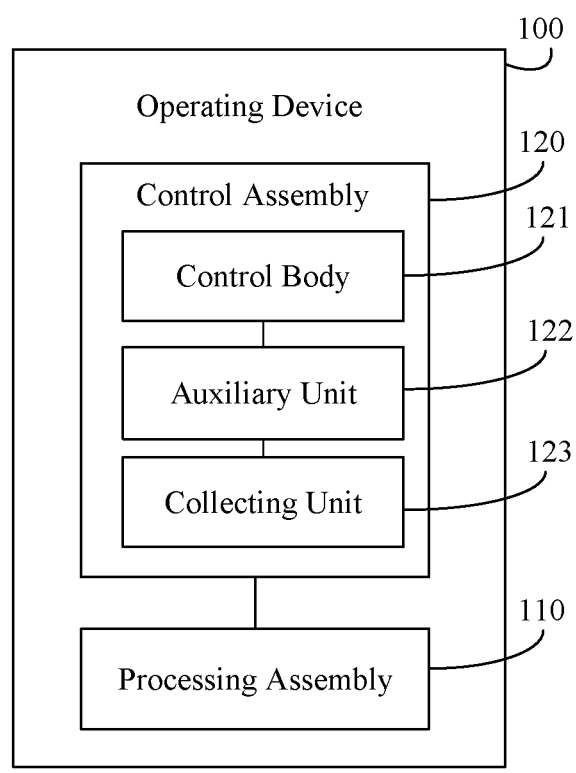
FIG. 1A is a structural diagram of an operating device provided by an embodiment of the present disclosure.

FIG. 1A is a structural diagram of an operating device 100 provided by an embodiment of the present disclosure. Said operating device 100 may comprise a processing assembly 110 and a control assembly 120. The control assembly 120 may comprise a control body 121, an auxiliary unit 122 and a collecting unit 123. The control body 121 can be a component to be controlled in the operating device. For example, in case the operating device is a wheelchair, the control body 121 can be a mechanical component that can directly enable the wheelchair to perform actions like moving forward or moving backward. The processing component typically can be a component capable of data analysis and processing such as a processor, a micro-processor and an integrated circuit, which is not limited herein. The auxiliary unit 122 can be arranged on the control body 121. Limbs of the user can be put on the auxiliary unit 122. The collecting unit 123 can be arranged on the limb of the user.

The collecting unit 123 can be configured to collect trembling signals indicating limb trembling of the user and to transmit the trembling signals to the processing assembly 110.

The processing assembly 110 can be configured to generate driving signals according to the trembling signals and transmit said driving signals to the auxiliary unit 122.

The auxiliary unit 122 can be configured to keep a motion state of said auxiliary unit 122 to be the same as the limb trembling state of the user according to the driving signals.

In the operating device provided in the embodiment of the present disclosure, the collecting unit of the control assembly of the operating device can transmit the collected trembling signals indicating limb trembling of the user to the processing assembly, and the processing assembly generates driving signals according to said trembling signals and transmits said driving signals to the auxiliary unit, so that according to said driving signals, the motion state of the auxiliary unit is kept to be the same as the limb trembling state of the user so as to eliminate interference to the control body by the trembling signals. Therefore, compared to the prior art, the auxiliary unit can eliminate the acting force of the limb of the user on the control body owing to morbid tremor, thereby avoiding that the action achieved by the control body is inconsistent with the intention of operation of the user, as a result, the operating device becomes more reliable.

The trembling signals collected by the collecting unit are signals of irregular limb trembling caused by morbid tremor (e.g. Parkinson syndrome, sequelae of epilepsy and cerebral palsy) of the user. The collecting unit can also collect motion signals indicating limb motions of the user, said motion signals include trembling signals and autonomous motion signals (the autonomous motion signals indicating the intention of operation of the user). The collecting unit transmits the collected motion signals to the processing assembly which analyzes and processes said motion signals to separate the trembling signals, and then generates driving signals according to said trembling signals. That is, the collecting unit in the embodiment of the present disclosure can either directly obtain the irregular trembling signals, or derive the irregular trembling signals from the collected motion signals, which is not limited by the embodiment of the present disclosure. In addition, said motion signals may further include other signals generated by limb motions than the trembling signals and the autonomous motion signals, and if said signals are collected by the collecting unit, they can be directly filtered out.

As an example, the collecting unit can be a patch sensor. The operating device provided in the embodiment of the present disclosure can be a wheelchair.

Figure 1B:
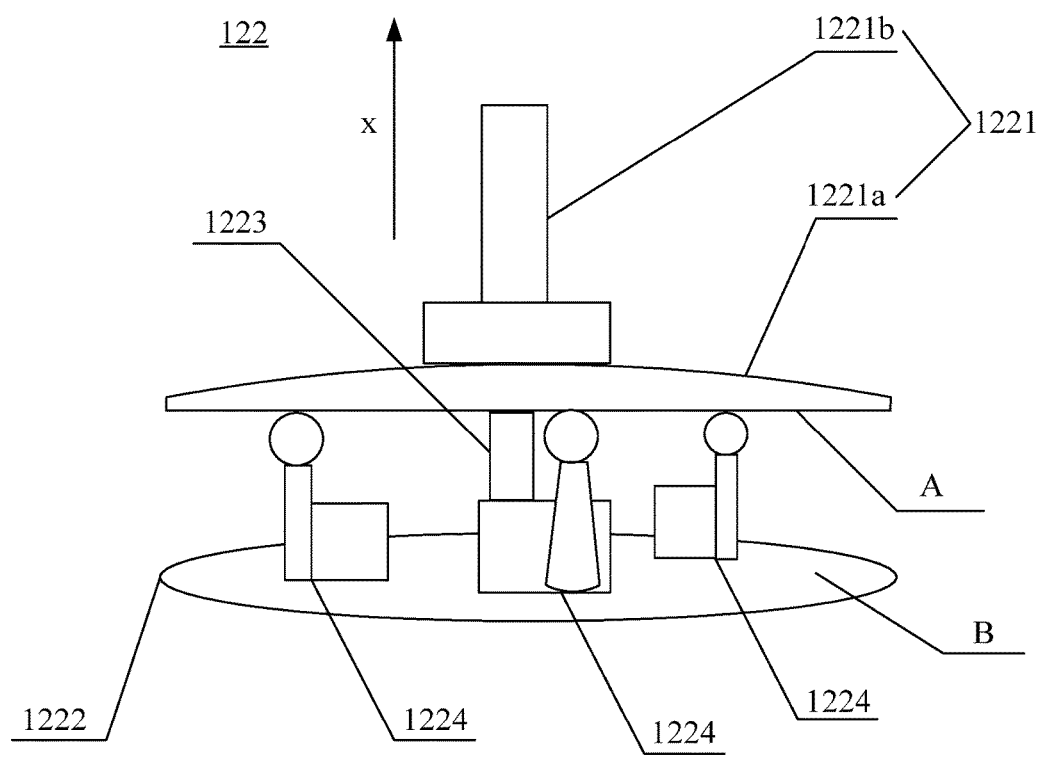
FIG. 1B is a structural diagram of an auxiliary unit provided by an embodiment of the present disclosure.

In certain exemplary embodiments, as shown in FIG. 1B, the auxiliary unit 122 may include a handrail 1221, a baseboard 1222, a hinge unit 1223 and at least three deflection units 1224.

The handrail 1221 may include a handrail chassis 1221*a* and a joystick 1221*b* connected thereto. A length direction of said joystick 1221*b* (direction indicated by x as shown in FIG. 1B) can be perpendicular to a surface A of the handrail chassis 1221*a*. Said joystick 1221*b* is configured to receive limb operations of the user. The surface A of the handrail chassis 1221*a* is parallel to a surface B of the baseboard 1222. In certain exemplary embodiments, the surface of the handrail chassis and the surface of the baseboard can both be circular. For example, the baseboard can be made of aluminum.

The hinge unit 1223 is located at the middle of a column formed by the handrail chassis 1221*a* and the baseboard 1222. The hinge unit 1223 is hinged to the handrail chassis 1221*a* and is fixedly connected to the baseboard 1222.

The at least three deflection units 1224 are inside the column formed by the handrail chassis 1221*a* and the baseboard 1222 and are distributed around the hinge unit 1223. The at least three deflection units 1224 are configured to deflect according to the driving signals, so that the motion state of the handrail 1221 remains to be the same as the limb trembling state of the user. As an example, the number of deflection units can be three. By providing three deflection units, the handrail chassis can have freedom of rotation in directions of x-axis, y-axis and z-axis. In this way, when the deflection units deflect according to the driving signals, an effect that the auxiliary unit completely counteracts irregular limb trembling actions can be achieved.

Figure 1C:
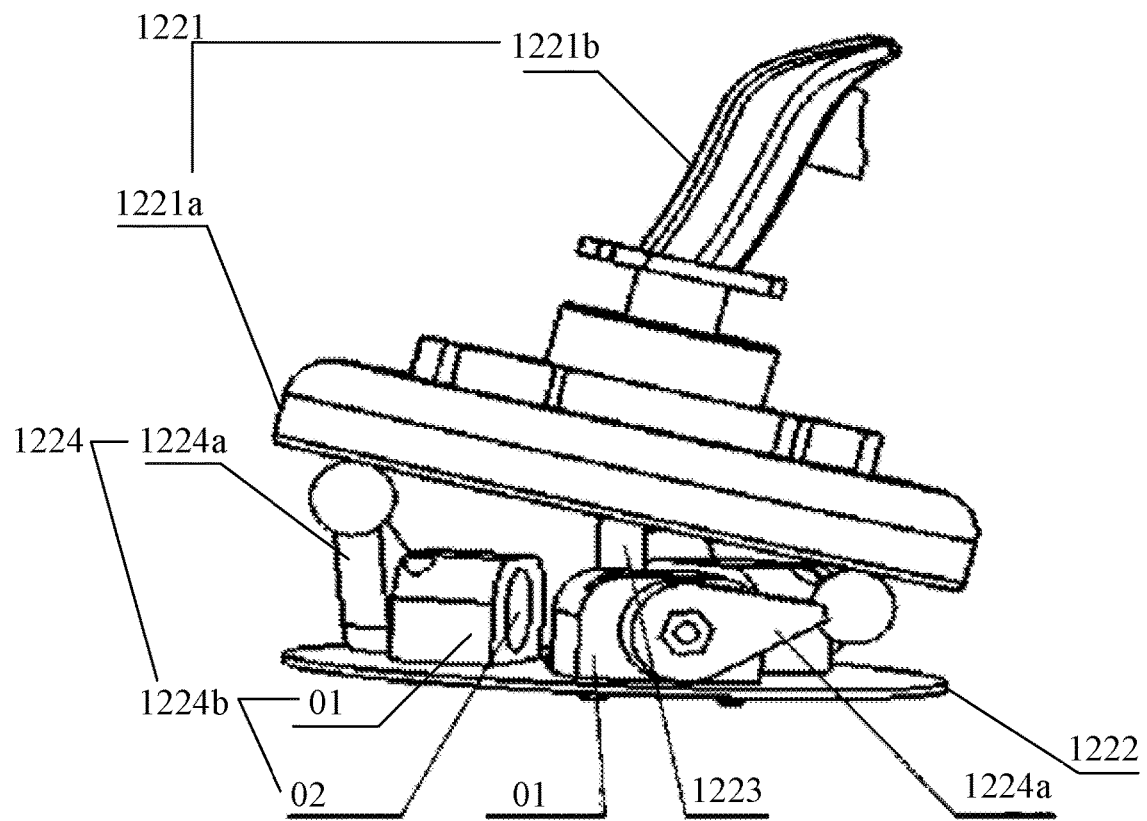
FIG. 1C is a structural diagram of another auxiliary unit provided by an embodiment of the present disclosure.

In certain exemplary embodiments, as shown in FIG. 1C, each deflection unit 1224 includes a rotating sub-unit 1224*a* and a driving sub-unit 1224*b*.

The rotating sub-unit 1224*a* is in point and plane contact with the handrail chassis 1221*a*, and is in fixed connection to the driving sub-unit 1224*b*. Said driving sub-unit 1224*b* is configured to rotate according to the driving signals so as to drive the rotating sub-unit 1224*a* to deflect.

In certain exemplary embodiments, as shown in FIG. 1C, the rotating sub-unit 1224*a* can be a cam. The driving sub-unit 1224*b* can comprise a motor bearing 01 and a motor 02 arranged in said motor bearing 01.

Said motor bearing 01 is fixedly connected to the baseboard 1222. Said motor 02 rotates according to the driving signals to drive said cam (i.e. the rotating sub-unit 1224*a*) to deflect. The operating device controls a plurality of motors to rotate so as to drive the cam to rotate, thereby enabling rotations and synthesized motions of the handrail chassis 1221*a* along x-axis, y-axis and z-axis in a three-dimensional space, so that the motion state of the auxiliary unit remains to be the same as the limb trembling state of the user.

Figure 1D:
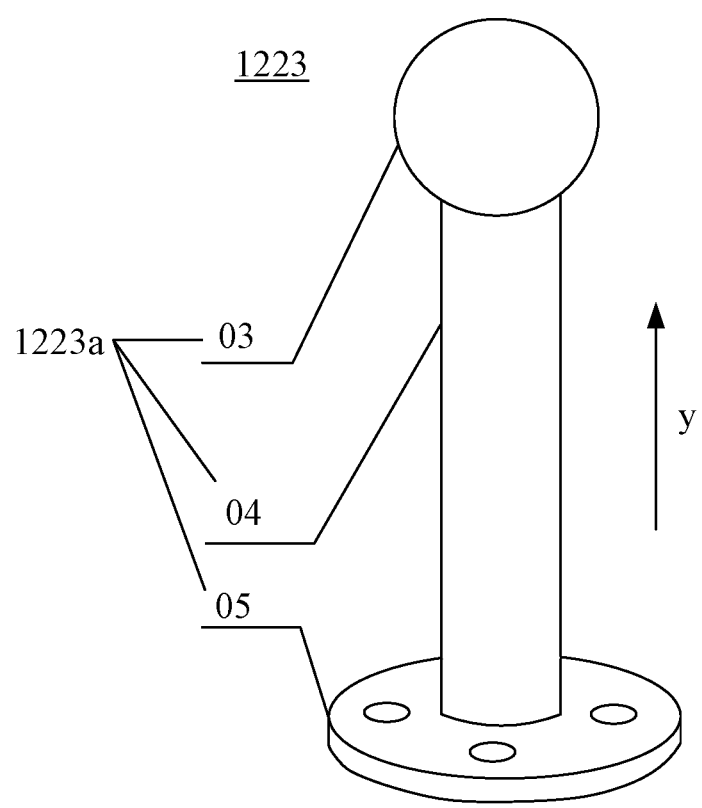
FIG. 1D is a structural diagram of a hinge unit provided by an embodiment of the present disclosure.
Figure 1E:
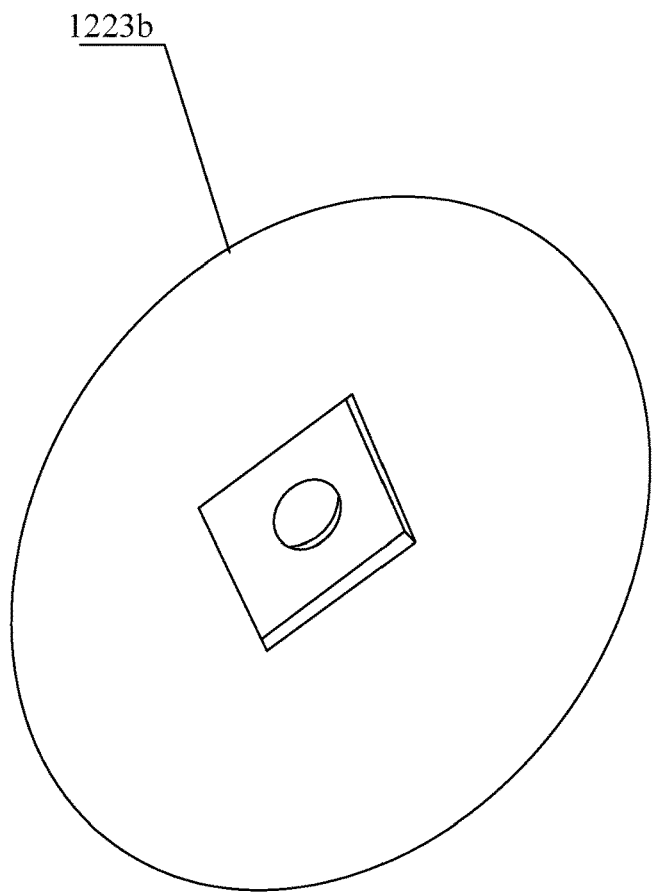
FIG. 1E is a top view of a hinge bearing provided by an embodiment of the present disclosure.
Figure 1F:
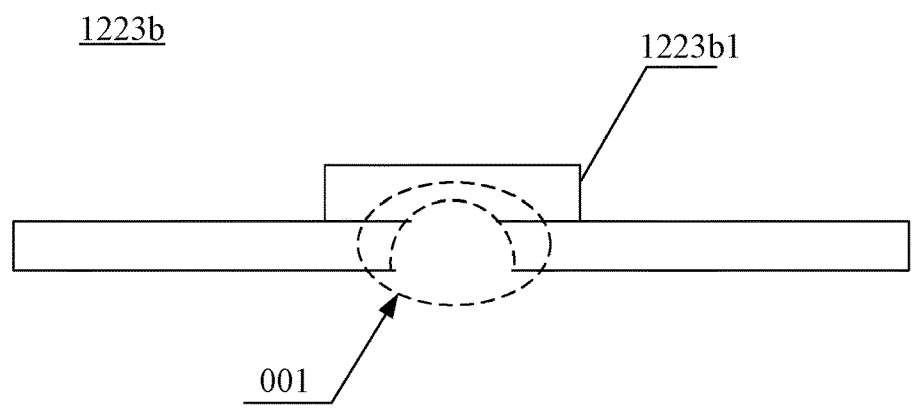
FIG. 1F is a side view of a hinge bearing provided by an embodiment of the present disclosure.

As shown in FIG. 1D, the hinge unit 1223 comprises a hinge frame 1223*a*, and a hinge bearing 1223*b* (as shown in FIG. 1E) is arranged between said hinge frame 1223*a* and the handrail chassis 1221*a*. Said hinge bearing 1223*b* is fixedly connected to the handrail chassis. FIG. 1E is a top view of the hinge bearing, and FIG. 1F is a side view of the hinge bearing. As shown in FIG. 1F, the hinge bearing is a column with a boss 1223*b*1, and a center of a side of said boss 1223*b*1 facing away from the handrail chassis is a concave (an area indicated by 001 in FIG. 1F).

Specifically, as shown in FIG. 1D, said hinge frame 1223*a* comprises a first connector 03, a second connector 04 and a third connector 05 connected in turn.

The first connector 03 can be spherical in shape, and is in contact with the concave center of the boss of the hinge bearing. The handrail chassis of said operating device is hinged to the hinge frame through the spherical hinge, so that the handrail chassis moves more flexibly.

The second connector 04 can be cylindrical in shape, and a height direction thereof (direction indicated by y as shown in FIG. 1D) is perpendicular to the surface of the handrail chassis (i.e. 1221*a* as shown in FIG. 1B).

The third connector 05 can be cylindrical in shape, and a height direction thereof (direction indicated by y as shown in FIG. 1D) is perpendicular to the surface of the baseboard (i.e. 1222 in FIG. 1B). The third connector 05 is fixedly connected to the baseboard and is at the middle of the baseboard.

Figure 1G:
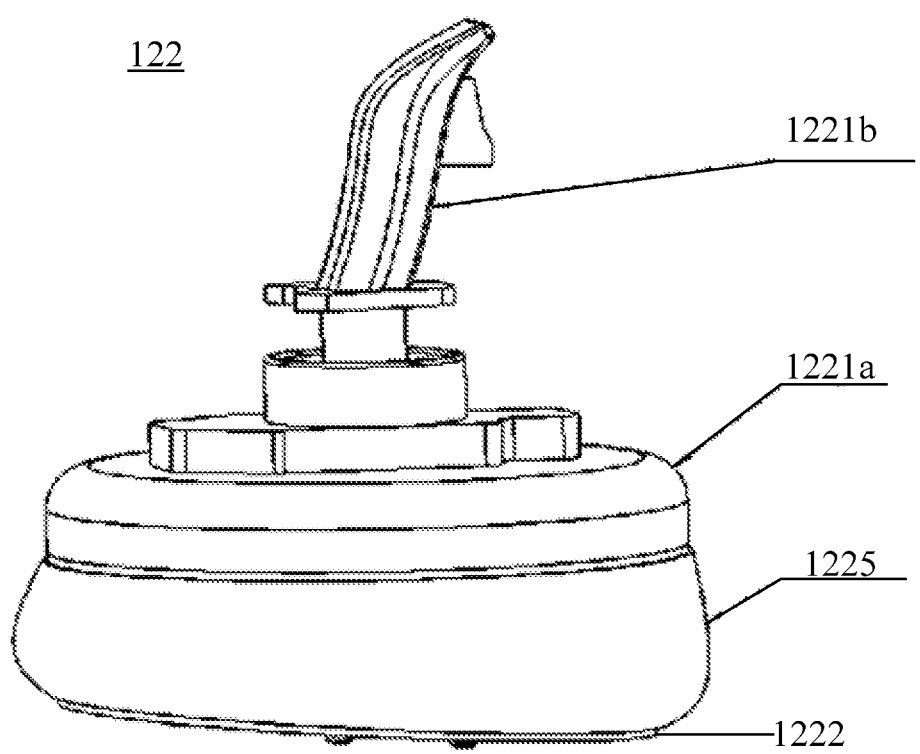
FIG. 1G is a structural diagram of still another auxiliary unit provided by an embodiment of the present disclosure.

In certain exemplary embodiments, as shown in FIG. 1G, the auxiliary unit 122 may further comprise a protection unit 1225 that can be made of an elastic material. Said protection unit 1225 can be arranged between the handrail chassis 1221*a* and the baseboard 1222, and encloses the hinge unit (not shown in FIG. 1G) and the at least three deflection units (not shown in FIG. 1G).

Figure 1H:
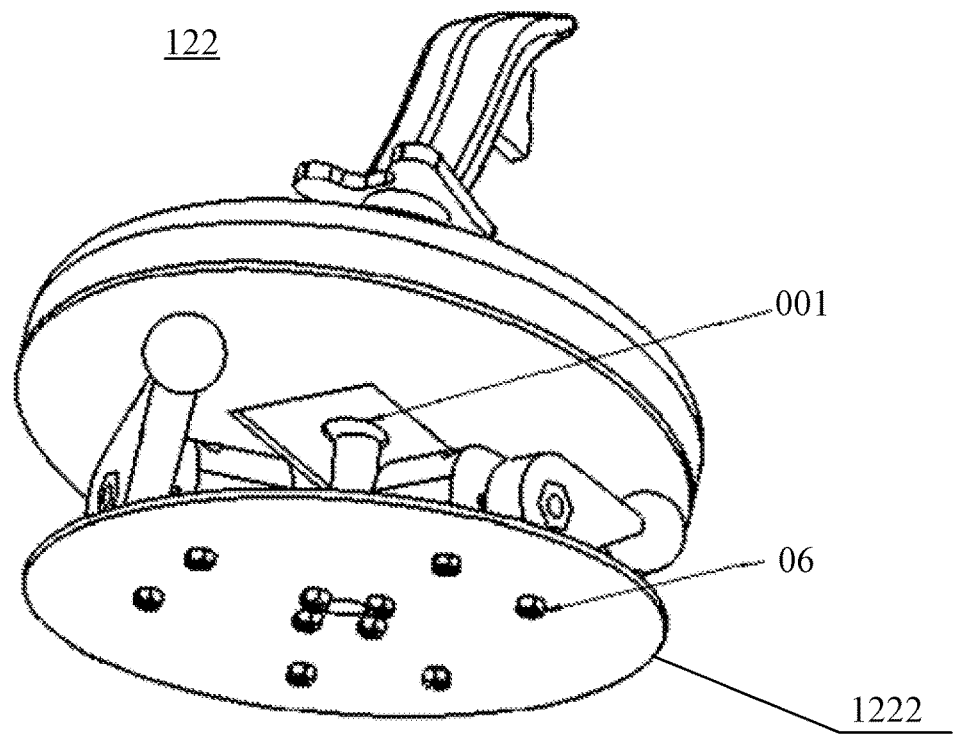
FIG. 1H is a structural diagram of yet another auxiliary unit provided by an embodiment of the present disclosure.

In certain exemplary embodiments, as shown in FIG. 1H, a bolt hole 06 is provided on the baseboard 1222, which is penetrated by a bolt. The auxiliary unit is fixed on the control body (not shown in FIG. 1H) through said bolt. The area indicated by 001 in FIG. 1H is the concave center of the boss of the hinge bearing. In practical application, the auxiliary unit provided in the embodiment of the present disclosure can be fixed on any operating device of the prior art, so that it may have the functions of the operating device provided in the embodiment of the present disclosure.

In certain exemplary embodiments, the processing assembly is further configured to transmit the pre-set adjustment signal to the auxiliary unit. Based on the adjustment signal, the motion state of said auxiliary unit can be made to be inconsistent with the limb trembling state of the user so as to correct limb trembling of the user. Said operating device has functions of active defibrillation and rehabilitation training, and it can help the user to perform rehabilitation training when being used by the user. Work modes of said operating device may include an active mode and a passive mode. In the active mode, the processing assembly transmits the pre-set adjustment signal to the auxiliary unit so as to adjust the motion state of the handrail chassis. The user holds the joystick in hand and adjusts and controls the joystick in a way of overcoming interference of the motion state of the handrail chassis according to his/her own will. By practicing repeatedly like this, recovery of body function can be realized.

In the passive mode, said operating device obtains trembling signals indicating limb trembling of the user and then adjusts motion parameters like speed and direction of the motor based on the trembling signals, so that the handrail chassis can rotate in the three directions of the x-axis, the y-axis and the z-axis by means of a point-surface constraint between the cam and the handrail chassis and a hinge constraint between the hinge unit and the handrail chassis, as a result, the motion state of the handrail chassis is the same as the morbid limb trembling state of the user. When the motion state of the handrail chassis is the same as the morbid limb trembling state of the user, the control body can accurately obtain the main operating actions of the user (said operating actions representing the operation intention of the user), thereby achieving the target actions accurately.

It shall be noted that when the user is using said operating device, trembling signals indicating limb trembling of the user can be actively recorded so as to provide a basis for judging the development trend of the disease.

The control body in embodiment of the present disclosure can be controlled by the processing assembly or be directly operated by limbs of the user. In case that the control body is controlled by the processing assembly, the processing assembly can receive instructions triggered by the user and transmit said instructions to the control body, which controls the operating device to achieve the target action according to said instructions. In case that the control body is directly operated by the limbs of the user, it can achieve corresponding target actions under limb operations of the user. For example, in case that the operating device is a wheelchair, if the control assembly is not directly operated by the limbs of the user, it can move forward or backward according to instructions sent by the processing assembly. No matter the control body is controlled by the processing assembly or controlled directly by limbs of the user, the operating device provided by the embodiment of the present disclosure can use the auxiliary unit to eliminate interference to the control body caused by the irregular trembling signals of the user, so that the control body can accurately receive instructions triggered by the user or accurately receive the autonomous motion signals corresponding to the main operating actions of the user so as to achieve corresponding target actions.

In certain exemplary embodiments, the processing assembly is further configured to transmit the pre-obtained autonomous motion signals to the control body after transmitting the driving signals to the auxiliary unit, so that the operating device can achieve the target actions indicated by the autonomous motion signals. Said autonomous motion signals indicate the intention of operation of the user. Said autonomous motion signals can be signals indicating autonomous motions of limbs of the user as collected by the collecting unit. In addition, the processing assembly is further configured to transmit the pre-obtained instructions triggered by the user to the control body, so that the operating device can achieve the target actions in compliance with the intention of operation of the user.

It shall also be pointed out that in the prior art, morbid tremor of human body is mainly treated by means of surgical operations and nerve suppressive drugs, but said means of treatment is harmful for human body and is riskier. Besides, patients of morbid tremor are mostly patients over 60 years of age, and these patients are not suitable for surgical treatment. The operating device provided by the embodiment of the present disclosure can effectively help such patients to achieve the target actions and assist them in their operating actions.

In summary, in the operating device provided by the embodiment of the present disclosure, the collecting unit of the control assembly of said operating device can transmit the collected trembling signals to the processing assembly, and the processing assembly generates driving signals according to said trembling signals and transmits the driving signals to the auxiliary unit, so that the auxiliary unit can keep its motion state to be the same as the limb trembling state of the user according to the driving signals, thereby eliminating interference to the control body by the trembling signals. Therefore, compared to the prior art, the auxiliary unit can eliminate the acting force of the morbid trembling of the limbs of the user on the control body, and avoid that the actions achieved by the control body are inconsistent with the intention of operation of the user. Moreover, said operating device can also correct limb trembling of the user, thus improving reliability of the operating device.

Figure 2:
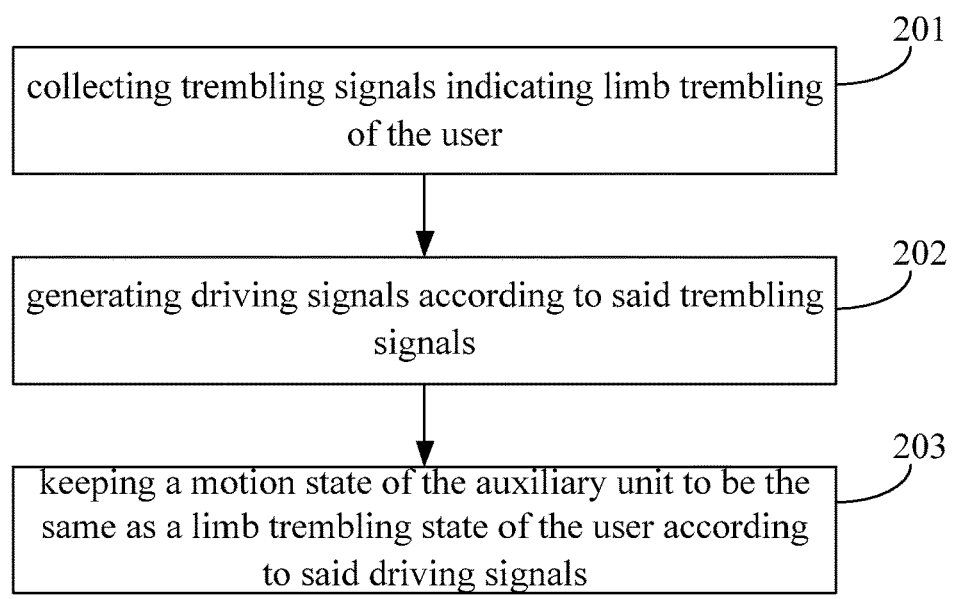
FIG. 2 is a flow chart of an operating method provided by an embodiment of the present disclosure.

FIG. 2 is a flow chart of an operating method provided by an embodiment of the present disclosure, said operating method can, for example, be carried out in conjunction with the operating device as shown in FIG. 1A or FIG. 1B. Said method may comprise:

step 201: collecting trembling signals indicating limb trembling of the user;

step 202: generating driving signals according to said trembling signals;

step 203: keeping a motion state of the auxiliary unit to be the same as a limb trembling state of the user according to said driving signals.

In the operating method provided in the embodiment of the present disclosure, driving signals can be generated according to the collected trembling signals and the motion state of the auxiliary unit can be kept to be the same as the limb trembling state of the user according to said driving signals so as to eliminate interference to the control body by the trembling signals. Compared to the prior art, the auxiliary unit can eliminate the acting force of the morbid trembling of the limbs of the user on the control body, and avoid that the actions achieved by the control body are inconsistent with the intention of operation of the user, thus improving reliability of the operating device.

Figure 3A:
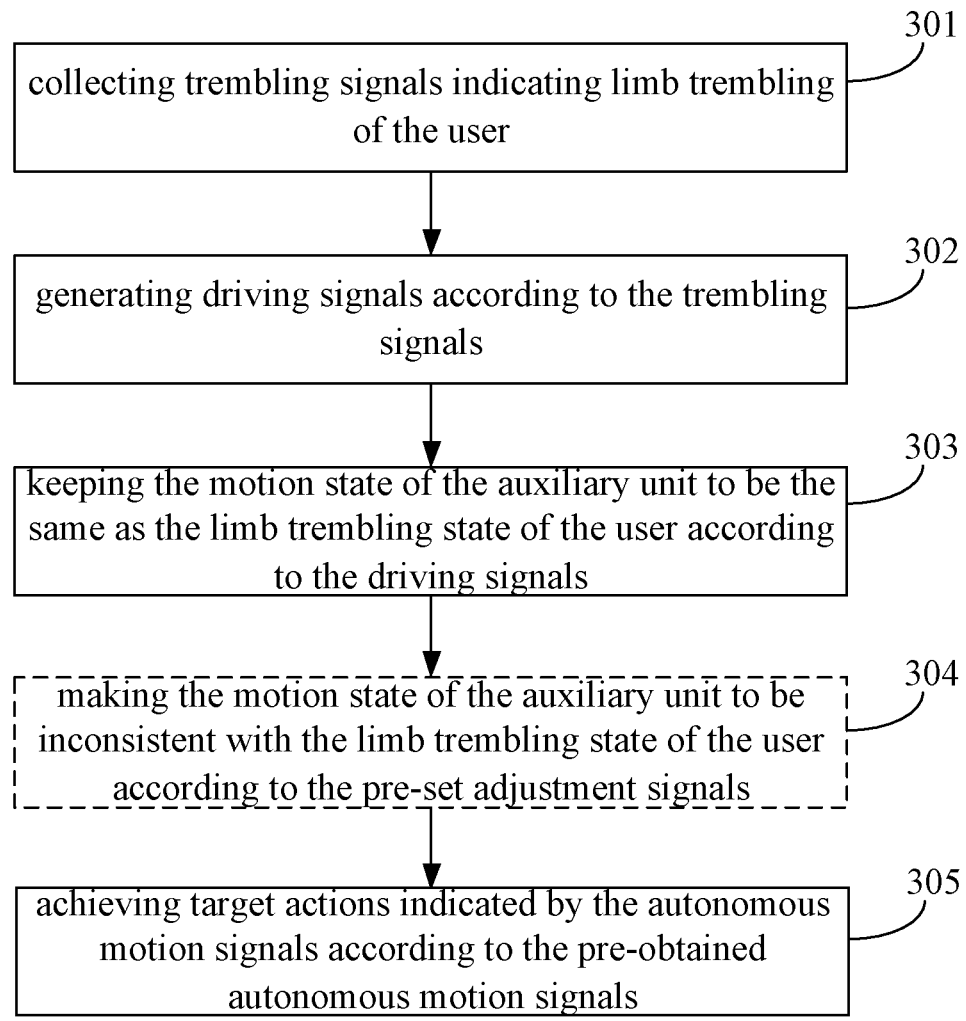
FIG. 3A is a flow chart of another operating method provided by an embodiment of the present disclosure.

FIG. 3A is a flow chart of another operating method provided by an embodiment of the present disclosure. Said method may comprise step 301: collecting trembling signals indicating limb trembling of the user. For example, the collecting unit can be used for collecting trembling signals indicating limb trembling of the user.

Figure 3B:
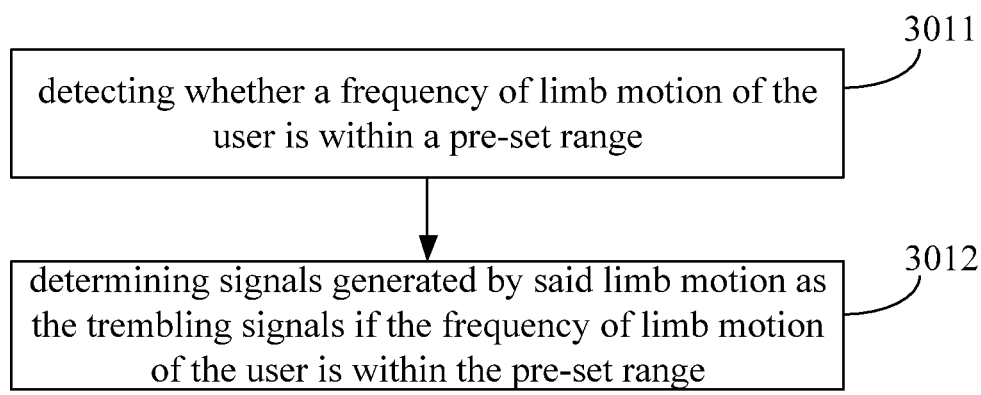
FIG. 3B is a flow chart of a method for collecting trembling signals provided by an embodiment of the present disclosure.

In certain exemplary embodiments, as shown in FIG. 3B, step 301 may include step 3011: detecting whether a frequency of limb motion of the user is within a pre-set range; and step 3012: determining signals generated by said limb motion as the trembling signals if the frequency of limb motion of the user is within the pre-set range.

The irregular limb trembling actions caused by morbid tremor (e.g. Parkinson syndrome, sequelae of epilepsy and cerebral palsy) of the user are different from normal limb actions in frequency. For example, the frequency of the trembling actions might be higher than the frequency of the normal actions. Thus, by detecting whether the frequency of limb motion of the user is within the pre-set range, it can be determined whether the signals generated by the limb motions are irregular trembling signals or not. If it is detected that the frequency of limb motion of the user is within the pre-set range, then the signals generated by the limb motions can be determined as trembling signals, so that driving signals can be generated according to the trembling signals.

It shall be noted that said method can comprise first collecting motion signals indicating limb motions of the user, which generally include trembling signals and autonomous motion signals indicating the intention of operation of the user; then analyzing and processing said motion signals to separate the trembling signals; and finally generating the driving signals according to the trembling signals. In addition, said motion signals may further include other signals generated by limb motions than the trembling signals and the autonomous motion signals. When said other signals are collected, they can be directly filtered out. The embodiment of the present disclosure does not limit the way of obtaining the trembling signals.

In certain exemplary embodiments, step 301 may further include: collecting trembling signals indicating limb trembling of the user through a patch sensor. In addition to the patch sensor, in the operating method provided by the embodiment of the present disclosure, any other sensor having the collecting and calculating functions or having the collecting function to collect trembling signals indicating limb trembling of the user can also be used, which is not limited by the embodiment of the present disclosure.

Said method further comprises step 302: generating driving signals according to the trembling signals. For example, the processing assembly can be used for generating driving signals according to the trembling signals.

Said method further comprises step 303: keeping the motion state of the auxiliary unit to be the same as the limb trembling state of the user according to the driving signals. By keeping the motion state of the auxiliary unit to be the same as the limb trembling state of the user according to the driving signals, interference to the control body of the operating device caused by the trembling signals can be eliminated. For example, the auxiliary unit can be used for keeping the motion state of the auxiliary unit to be the same as the limb trembling state of the user according to the driving signals.

In certain exemplary embodiments, said method further comprises step 304: making the motion state of the auxiliary unit to be inconsistent with the limb trembling state of the user according to the pre-set adjustment signals.

Specifically, the processing assembly can be used to make the motion state of the auxiliary unit to be inconsistent with the limb trembling state of the user according to the pre-set adjustment signals, thereby correcting limb trembling of the user.

Said method further comprises step 305: achieving target actions indicated by the autonomous motion signals according to the pre-obtained autonomous motion signals.

Said autonomous motion signals are used for indicating the intention of operation of the user. Said autonomous motion signals can be signals indicating autonomous motions of limbs of the user as collected by the collecting unit. In addition, said method can also comprise achieving target actions consistent with the intention of operation of the user according to the pre-obtained instructions triggered by the user.

It shall be noted that the order of steps of the operating method provided in the embodiment of the present disclosure is not restrictive, but it can be adjusted as desired, and the number of steps can also be changed according to the actual situation. Various changes of the method that are easily conceivable by those skilled in the art within the technical scope of the present disclosure shall be included in the protection scope of the present disclosure.

In summary, in the operating method provided by the embodiment of the present disclosure, driving signals can be generated according to the collected trembling signals indicating limb trembling of the user and then keep the motion state of the auxiliary unit to be the same as the limb trembling state of the user according to the driving signals to thereby eliminate interference to the control body by the trembling signals, thus compared to the prior art, the auxiliary unit can eliminate the acting force of the morbid trembling of the limbs of the user on the control body, and avoid that the actions achieved by the control body are inconsistent with the intention of operation of the user. Moreover, said operating device can also correct limb trembling of the user. Therefore, reliability of the operating device is improved.

The above described are merely exemplary embodiments of the present disclosure, while they do not intend to limit the present disclosure. Any modification, equivalent substitution and improvement made under the spirit and principle of the present disclosure shall be included in the protection scope of the present disclosure.

The invention claimed is:

1. An operating device, comprising:
   a processing assembly; and
   a control assembly comprising a control body, an auxiliary unit and a collecting unit;
   wherein the auxiliary unit is arranged on the control body, a limb of a user is put on said auxiliary unit, and the collecting unit is arranged on the limb of the user; and wherein
   said collecting unit is configured to collect trembling signals indicating limb trembling of the user, and transmit said trembling signals to the processing assembly;
   said processing assembly is configured to generate driving signals according to said trembling signals and transmit said driving signals to the auxiliary unit;
   said auxiliary unit is configured to keep a motion state of said auxiliary unit to be the same as a limb trembling state of the user according to said driving signals.

2. The operating device according to claim 1, wherein said auxiliary unit comprises: a handrail, a baseboard, a hinge unit and at least three deflection units, wherein
   said handrail is provided with a handrail chassis and a joystick connected to said handrail chassis, a length direction of said joystick is perpendicular to a surface of the handrail chassis, said joystick is configured to receive limb operations of the user, and the surface of the handrail chassis is parallel to a surface of the baseboard;
   said hinge unit is located at the middle of a column formed by the handrail chassis and the baseboard and is hinged to the handrail chassis, and said hinge unit is fixedly connected to the baseboard;

said at least three deflection units are inside the column formed by the handrail chassis and the baseboard and distributed around the hinge unit, and are configured to deflect according to the driving signals, so that the motion state of the handrail remains to be the same as the limb trembling state of the user.

3. The operating device according to claim 2, wherein each of said deflection units include a rotating sub-unit and a driving sub-unit, and wherein said rotating sub-unit is in point and plane contact with the handrail chassis and is in fixed connection to said driving sub-unit, and said driving sub-unit is configured to rotate according to the driving signals so as to drive said rotating sub-unit to deflect.

4. The operating device according to claim 3, wherein said rotating sub-unit comprises a cam, and said driving sub-unit comprises a motor bearing and a motor arranged in said motor bearing; and wherein said motor bearing is fixedly connected to said baseboard, and said motor is configured to rotate according to the driving signals so as to drive said cam to deflect.

5. The operating device according to claim 2, wherein said hinge unit comprises a hinge frame, and a hinge bearing is provided between said hinge frame and said handrail chassis, said hinge bearing is fixedly connected to said handrail chassis, said hinge bearing is a column with a boss, and a center of a side of said boss facing away from the handrail chassis is concave in shape.

6. The operating device according to claim 5, wherein said hinge frame comprises a first connector, a second connector and a third connector connected in turn; wherein the first connector is spherical in shape, and is in contact with the concave center of the boss;

the second connector is cylindrical in shape, and a height direction thereof is perpendicular to the surface of the handrail chassis; and the third connector is cylindrical in shape, and a height direction thereof is perpendicular to the surface of the baseboard, the third connector being fixedly connected to the baseboard and being at the middle of the baseboard.

7. The operating device according to claim 2, wherein said auxiliary unit further comprises:

a protection unit made of an elastic material, wherein said protection unit is arranged between the handrail chassis and the baseboard, and encloses the hinge unit and the at least three deflection units.

8. The operating device according to claim 2, wherein a bolt hole is provided on the baseboard, which is penetrated by a bolt so that said auxiliary unit is fixed on the control body.

9. The operating device according to claim 2, wherein said processing assembly is further configured to transmit a pre-set adjustment signal to said auxiliary unit; and said auxiliary unit is further configured to make the motion state of said auxiliary unit to be inconsistent with the limb trembling state of the user according to said adjustment signal.

10. The operating device according to claim 1, wherein said collecting unit comprises a patch sensor.

11. The operating device according to claim 2, wherein the surface of the handrail chassis and the surface of the baseboard are both circular.

12. The operating device according to claim 2, wherein said baseboard is made of aluminum.

13. The operating device according to claim 1, wherein said processing assembly is further configured to transmit pre-obtained autonomous motion signals to the control body after transmitting the driving signals to the auxiliary unit, so that the operating device achieves the target action indicated by the autonomous motion signals, said autonomous motion signals indicating the intention of operating of the user.

14. An operating method carried out by the operating device according to claim 1, comprising:

collecting trembling signals indicating limb trembling of the user;

generating driving signals according to said trembling signals;

keeping a motion state of the auxiliary unit to be the same as a limb trembling state of the user according to said driving signals.

15. The method according to claim 14, wherein said method further comprises:

making the motion state of said auxiliary unit to be inconsistent with the limb trembling state of the user according to a pre-set adjustment signal.

16. The method according to claim 14, wherein said collecting trembling signals indicating limb trembling of the user comprises:

detecting whether a frequency of limb motion of the user is within a pre-set range;

determining signals generated by said limb motion as the trembling signals if the frequency of limb motion of the user is within the pre-set range.

17. The method according to claim 14, wherein said collecting trembling signals indicating limb trembling of the user comprises:

collecting trembling signals indicating limb trembling of the user through a patch sensor.

18. The method according to claim 14, wherein said method further comprises:

achieving the target action indicated by the autonomous motion signals according to the pre-obtained autonomous motion signals, said autonomous motion signals indicating the intention of operation of the user.

19. The method according to claim 15, wherein said collecting trembling signals indicating limb trembling of the user comprises:

collecting trembling signals indicating limb trembling of the user through a patch sensor.

20. The method according to claim 15, wherein said method further comprises:

achieving the target action indicated by the autonomous motion signals according to the pre-obtained autonomous motion signals, said autonomous motion signals indicating the intention of operation of the user.

* * * * *